(12) United States Patent
Piazza et al.

(10) Patent No.: US 9,388,139 B2
(45) Date of Patent: Jul. 12, 2016

(54) DERIVATIVES OF CELEBOXIB, USE THEREOF AND PREPARATION THEREOF

(75) Inventors: Gary A. Piazza, Mobile, AL (US); Ashraf H. Abadi, Cairo (EG)

(73) Assignees: German University, Cairo (EG); Southern Research Institute, Birmingham, AL (US)

( * ) Notice: Subject to any disclaimer, the term of this patent is extended or adjusted under 35 U.S.C. 154(b) by 0 days.

(21) Appl. No.: 14/005,462

(22) PCT Filed: Mar. 16, 2012

(86) PCT No.: PCT/US2012/029328
§ 371 (c)(1),
(2), (4) Date: Dec. 12, 2013

(87) PCT Pub. No.: WO2012/125884
PCT Pub. Date: Sep. 20, 2012

(65) Prior Publication Data
US 2014/0171477 A1    Jun. 19, 2014

Related U.S. Application Data

(60) Provisional application No. 61/453,795, filed on Mar. 17, 2011.

(51) Int. Cl.
*C07D 231/06* (2006.01)
*C07D 231/12* (2006.01)

(52) U.S. Cl.
CPC ............ *C07D 231/06* (2013.01); *C07D 231/12* (2013.01)

(58) Field of Classification Search
None
See application file for complete search history.

(56) References Cited

U.S. PATENT DOCUMENTS

| 6,323,226 | B1 | 11/2001 | Delgado, III et al. |
| 2004/0198826 | A1 | 10/2004 | Baiker et al. |
| 2007/0066651 | A1 | 3/2007 | Cuberes Altisen et al. |
| 2008/0300278 | A1 | 12/2008 | Torrens Jover et al. |

OTHER PUBLICATIONS

Levai, Synthesis of carboxylic acid derivatives of 2-pyrazolines, Arkivoc, 2007, 1, pp. 134-145.*
Mukai, On the syntheses and the optical properties of optically active 2-pyrazoline compounds, Can. J. Chem., 1979, 57, pp. 360-366.*

* cited by examiner

*Primary Examiner* — San-Ming Hui
*Assistant Examiner* — Andrew Lee
(74) *Attorney, Agent, or Firm* — Polsinelli PC

(57) ABSTRACT

Derivatives of celecoxib that lack cyclooxygenase inhibitory activity but have improved PDE5 inhibitory activity are provided along with pharmaceutical compositions containing them for the treatment or prevention of cancer. Such compounds are expected to have reduced toxicity compared with celecoxib and other cyclooxygenase inhibitors, and greater efficacy compared with conventional PDE5 inhibitors. Derivatives of celecoxib are also suitable for treating chronic inflammatory conditions, erectile dysfunction, pulmonary hypertension, congestive heart failure, and enhancement of cognitive function.

8 Claims, No Drawings

DERIVATIVES OF CELEBOXIB, USE THEREOF AND PREPARATION THEREOF

CROSS REFERENCE TO RELATED APPLICATIONS

This application is a National Phase filing under 35 U.S.C. §371 of PCT/US2012/029328 filed on Mar. 16, 2013; and this application claims the benefit of U.S. Provisional Application No. 61/453,795 filed on Mar. 17, 2011; the entire contents of all are hereby incorporated by reference.

FEDERALLY SPONSORED RESEARCH AND DEVELOPMENT

This invention was supported by Grant 1 RO1 CA148817-01A1 from the National Cancer Institute of the National Institutes of Health and the US Government has certain rights in the invention.

TECHNICAL FIELD

The present disclosure relates to certain derivatives of celecoxib. According to the present disclosure, the disclosed compounds lack COX-2 inhibitory activity but retain PDE5 inhibitory activity. The present disclosure also relates to pharmaceutical compositions comprising the disclosed derivatives of celecoxib, as well as a method of using the compounds for the treatment of cancer in a mammal. Also disclosed is a method for the preparation thereof. Disclosed derivatives of celecoxib are also suitable for treating chronic inflammatory conditions with reduced cardiovascular toxicity, erectile dysfunction, enhancement of cognitive functions, benign prostatic hyperplasia, pulmonary arterial hypertension and congestive heart failure.

BACKGROUND

Even though significant advances have occurred in the treatment of cancer, it still remains a major health concern. Cancer has been reported as the leading cause of death in the United States with one of every four Americans likely to be diagnosed with the disease[1].

Included among the known chemotherapeutic drugs are carmustine, doxorubicin, methotrexate, paclitaxel, cyclophosphamide, procarbazine, and vinblastine, to name only a few. However, many chemotherapeutic drugs also produce undesirable side effects in the patient[2,3].

Certain nonsteroidal anti-inflammatory drugs (NSAIDs) have been recognized to have broad anticancer activity in animal models alone and in combination with chemotherapy or radiation[4].

Cyclooxygenase 2 (COX-2) inhibitors are known to have cancer chemopreventive and therapeutic benefits. Their clinical use, however, is limited by cardiovascular toxicities including myocardial infarction and stroke. These toxicities result from COX-2 inhibition in endothelial cells and the suppression of prostacyclin, which has vasodilatory activity and can inhibit platelet aggregation. Previous studies suggest that the anticancer properties of COX-2 inhibitors may not involve COX-2, but rather involves the inhibition of phosphodiesterase 5 (PDE5) and elevation of the intracellular signaling molecule, cyclic GMP to selectively induce the apoptosis (programmed cell death) of tumor cells[5-7].

The present inventors have shown that the COX-2 inhibitor, celecoxib can inhibit PDE5 at concentrations that suppress tumor cell growth. Others have shown that the PDE5 inhibitory activity of celecoxib provides cardioprotective activity, which may explain why celecoxib has less cardiovascular toxicity compared with other COX-2 inhibitors, such as rofecoxib[8].

Notwithstanding the advances in treatments for cancer and other diseases there still remains room for improved drugs that are effective, while at the same time exhibiting reduced adverse side effects.

SUMMARY OF DISCLOSURE

The present disclosure relates to derivatives of celecoxib represented by the formula:

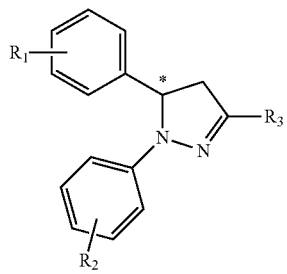

wherein $R_1$ is selected from the group consisting of —H, —F, —Cl, Br, dihalo, —$CH_3$, —$OCH_3$, —$OC_2H_5$, 3,4-O—$CH_2$—O—, —$NO_2$, and —OH;

R2 is selected from the group consisting of —COOH, —$SO_3H$, —CONHR (R is selected from the group consisting of —$CH_3$, —$C_2H_5$, —$C_3H_7$, and $C_4H_9$), —SO2-NHR (R is selected from the group consisting of —$CH_3$, —$C_2H_5$, —$C_3H_7$, and $C_4H_9$); and R3 is selected from the group consisting of -t-butyl, phenyl, methoxyphenyl, dimethoxyphenyl, and 4-halophenyl;

and pharmaceutically acceptable salts thereof, prodrugs thereof, solvates thereof and mixtures thereof.

It is understood that the compounds of the present disclosure relate to all optical isomers racemate and stereo-isomers at the various possible atoms of the molecule, unless specified otherwise Pyrazoline derivatives of celccoxib according to the present disclosure lack COX-2 and COX-1 inhibitory activity but retain or have improved PDE5 inhibitory activity and ability to inhibit neoplastic cell growth. Accordingly, also disclosed are methods of using the compounds of the present disclosure in treating or preventing cancer in a mammal.

Another aspect of this disclosure is concerned with methods of using the compounds in treating chronic inflammatory diseases such as inflammatory bowel disease and certain neurodegenerative diseases including Alzheimer's disease, dementia and enhancement of cognitive functions. The disclosed compounds are useful in the treatment of cardiovascular disorders like pulmonary arterial hypertension and congestive heart failure.

A still further aspect of this disclosure concerned with a method for preparing the above-disclosed compounds.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES

The present disclosure relates to derivatives of celecoxib represented by the formula:

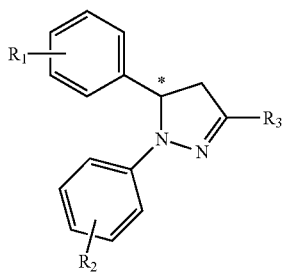

wherein $R_1$ is selected from the group consisting of —H, —F, —Cl, Br, dihalo, —$CH_3$, —$OCH_3$, —$OC_2H_5$, 3,4-O—$CH_2$—O—, —$NO_2$, and —OH;

$R_2$ is selected from the group consisting of —COOH, —$SO_3H$, —CONHR (R is selected from the group consisting of —$CH_3$, —$C_2H_5$, —$C_3H_7$, and $C_4H_9$), —$SO_2$-NHR (R is selected from the group consisting of —$CH_3$, —$C_2H_5$, —$C_3H_7$, and $C_4H_9$); and $R_3$ is selected from the group consisting of -t-butyl, phenyl, methoxyphenyl, dimethoxyphenyl, and 4-halophenyl;

and pharmaceutically acceptable salts thereof, prodrugs thereof, solvates thereof and mixtures thereof.

It is understood that the compounds of the present disclosure relate to all optical isomers racemate and stereo-isomers at the various possible atoms of the molecule, unless specified otherwise Preparations of prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Representative compounds according to the present disclosure can be prepared as shown below (Scheme 1). For simplicity, the below process shows only a $R_3$ substituent and the COOH derivative, it being understood that the other derivatives can be fabricated by the above process using the appropriate precursors as would be understood by those skilled in the art.

Scheme 1

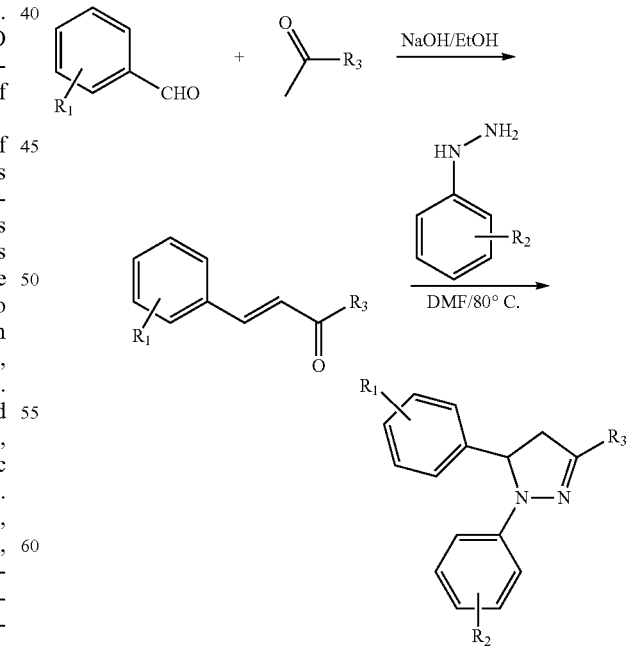

The following are representative compounds but non-limiting examples of the present disclosure:

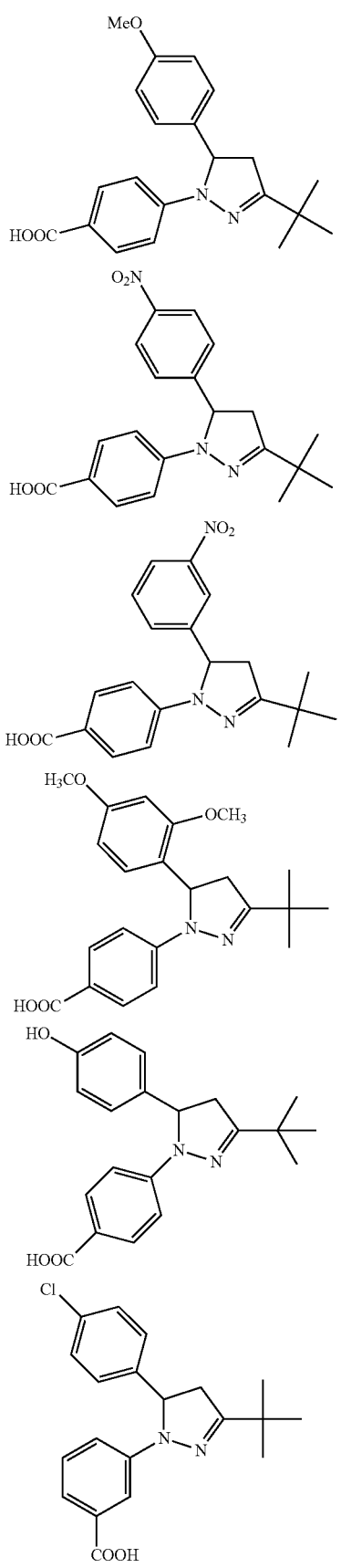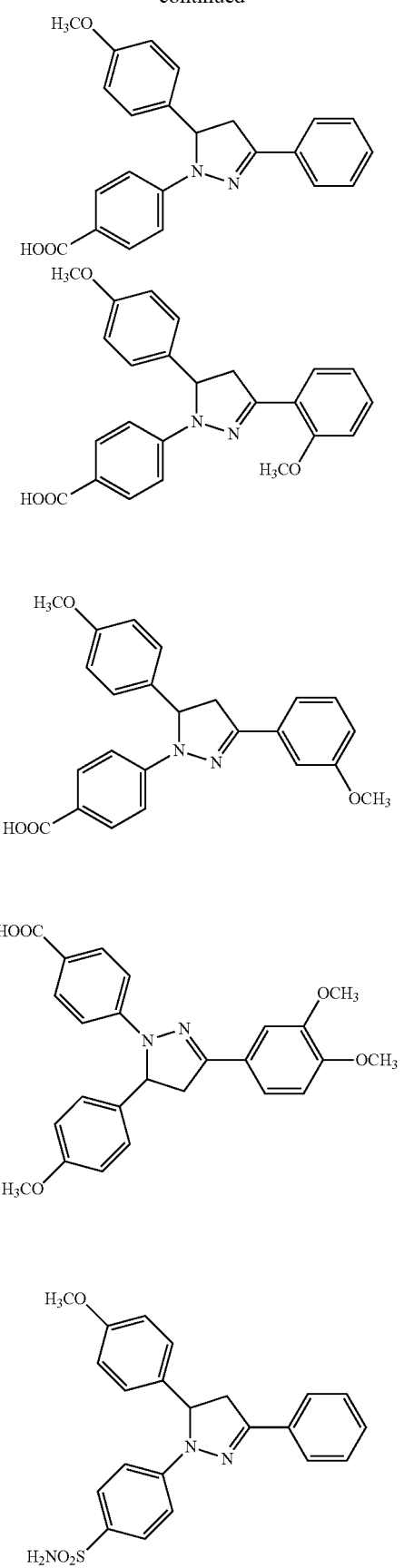

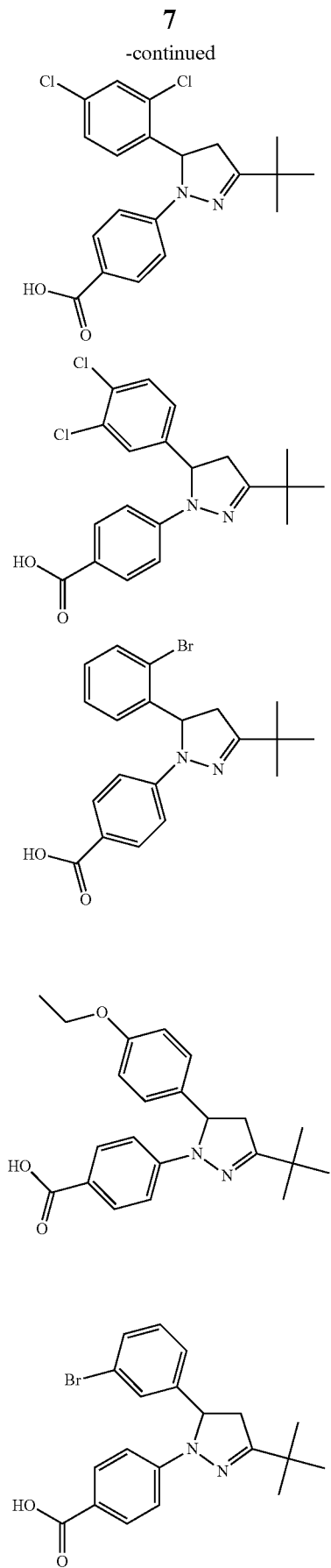
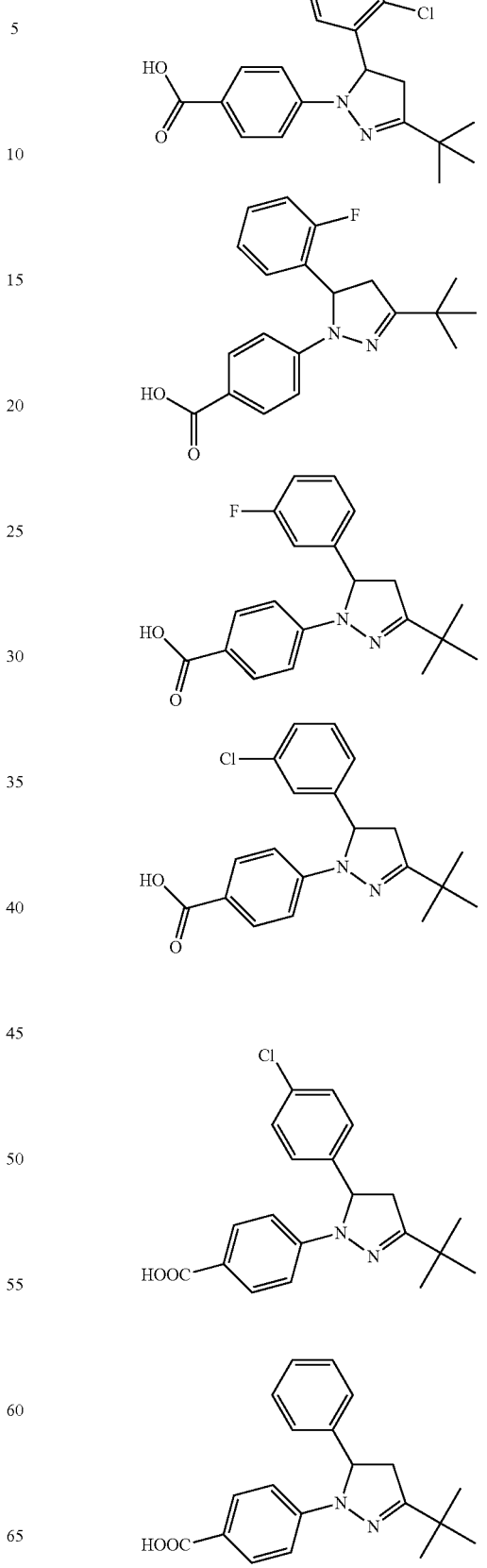

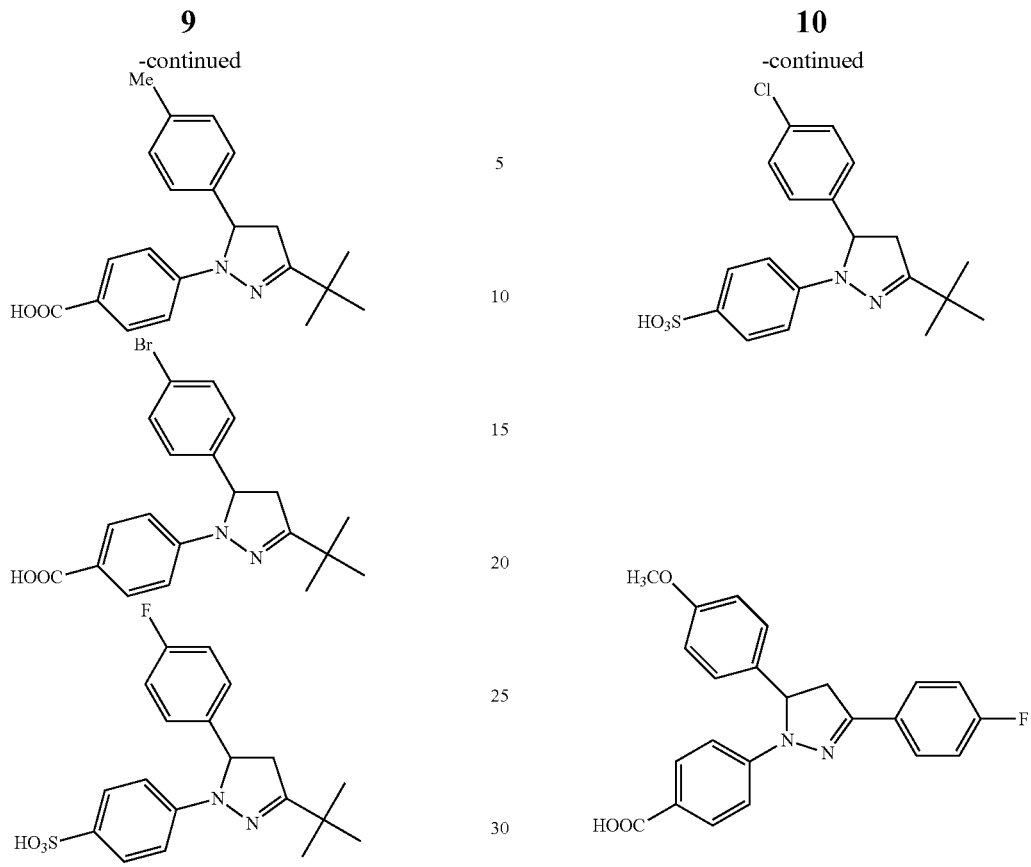
TABLE 1
Inhibitory effect of the exemplified compounds against PDE5, COX1, COX2, and growth of the human breast MDA-MB-231 and colorectal HT-29 tumor cell lines.
| Compound ID | Structure | IC$_{50}$ μM against PDE5 | IC$_{50}$ μM against COX1 | IC$_{50}$ μM against COX2 | IC$_{50}$ μM against MDA-MB-231 | IC$_{50}$ μM against HT-29 |
|---|---|---|---|---|---|---|
| 1 | 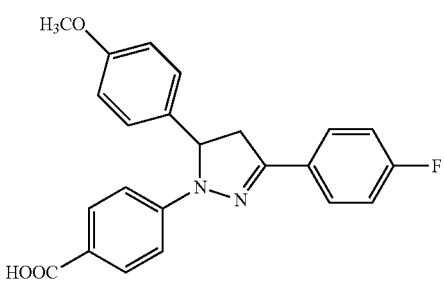 | 2.02 | >100 | >100 | >50 | >50 |
| 2 | 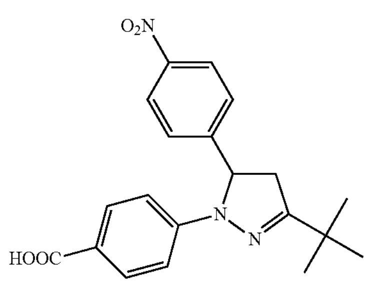 [SMILES: CC(C)(C)C1=NN(c2ccc(C(=O)O)cc2)C(c2ccc([N+](=O)[O-])cc2)C1] | 5.70 | >100 | >100 | >50 | >50 |

TABLE 1-continued

Inhibitory effect of the exemplified compounds against PDE5, COX1, COX2, and growth of the human breast MDA-MB-231 and colorectal HT-29 tumor cell lines.

| Compound ID | Structure | $IC_{50}$ µM against PDE5 | $IC_{50}$ µM against COX1 | $IC_{50}$ µM against COX2 | $IC_{50}$ µM against MDA-MB-231 | $IC_{50}$ µM against HT-29 |
|---|---|---|---|---|---|---|
| 3 | 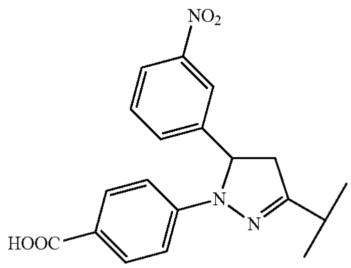 [SMILES: CC(C)C1=NN(c2ccc(C(=O)O)cc2)C(c2cccc([N+](=O)[O-])c2)C1] | 3.2 | >100 | >100 | >50 | >50 |
| 4 | 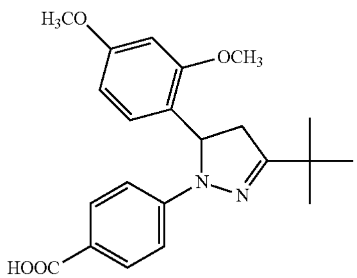 [SMILES: COc1ccc(C2CC(C(C)(C)C)=NN2c2ccc(C(=O)O)cc2)c(OC)c1] | 23.5 | >100 | >100 | >50 | >50 |
| 5 | 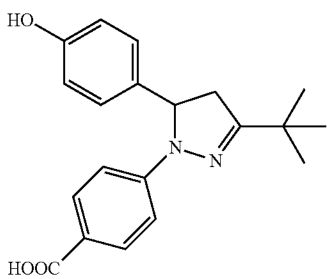 [SMILES: CC(C)(C)C1=NN(c2ccc(C(=O)O)cc2)C(c2ccc(O)cc2)C1] | 2.1 | >100 | >100 | >50 | >50 |
| 6 | 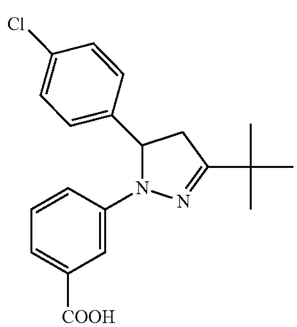 [SMILES: CC(C)(C)C1=NN(c2cccc(C(=O)O)c2)C(c2ccc(Cl)cc2)C1] | 9.9 | >100 | >100 | >50 | 39.9 |
| 7 | 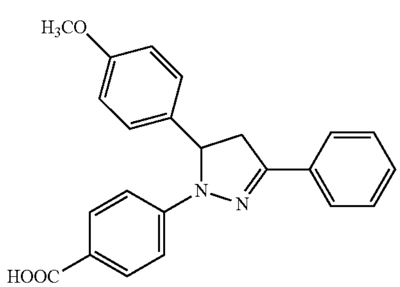 [SMILES: COc1ccc(C2CC(c3ccccc3)=NN2c2ccc(C(=O)O)cc2)cc1] | 1.2 | >100 | >100 | 48.0 | 36.7 |

TABLE 1-continued

Inhibitory effect of the exemplified compounds against PDE5, COX1, COX2, and growth of the human breast MDA-MB-231 and colorectal HT-29 tumor cell lines.

| Compound ID | Structure | $IC_{50}$ μM against PDE5 | $IC_{50}$ μM against COX1 | $IC_{50}$ μM against COX2 | $IC_{50}$ μM against MDA-MB-231 | $IC_{50}$ μM against HT-29 |
|---|---|---|---|---|---|---|
| 8 | 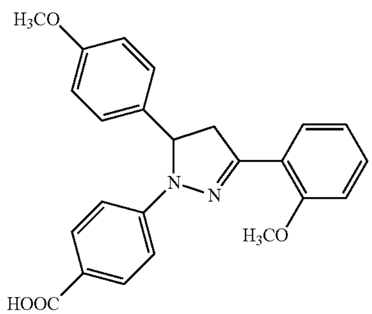 [SMILES: COc1ccc(C2CC(c3ccccc3OC)=NN2c2ccc(C(=O)O)cc2)cc1] | 3.2 | >100 | >100 | >50 | >50 |
| 9 | 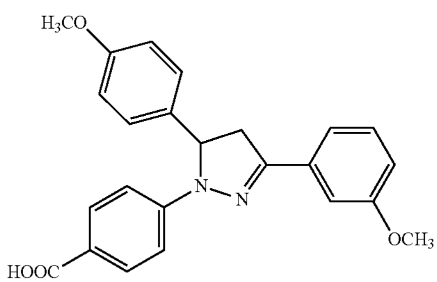 [SMILES: COc1ccc(C2CC(c3cccc(OC)c3)=NN2c2ccc(C(=O)O)cc2)cc1] | 1.8 | >100 | >100 | 45.6 | 25.9 |
| 10 | 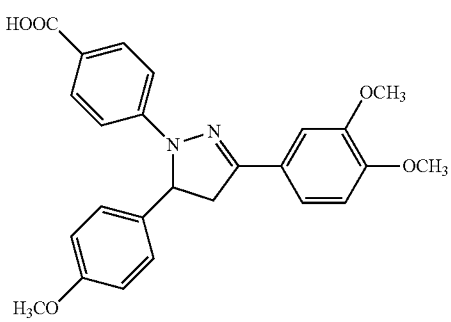 [SMILES: COc1ccc(C2CC(c3ccc(OC)c(OC)c3)=NN2c2ccc(C(=O)O)cc2)cc1] | 6.9 | >100 | >100 | >50 | 42.5 |
| 11 | 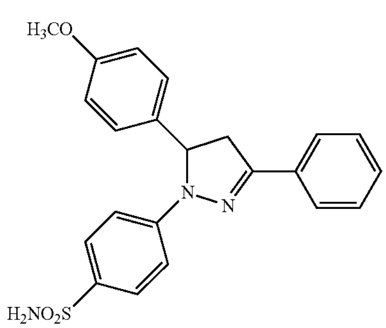 [SMILES: COc1ccc(C2CC(c3ccccc3)=NN2c2ccc(S(N)(=O)=O)cc2)cc1] | 3.8 | >100 | >100 | 27.6 | 15.6 |

TABLE 1-continued

Inhibitory effect of the exemplified compounds against PDE5, COX1, COX2, and growth of the human breast MDA-MB-231 and colorectal HT-29 tumor cell lines.

| Compound ID | Structure | IC$_{50}$ µM against PDE5 | IC$_{50}$ µM against COX1 | IC$_{50}$ µM against COX2 | IC$_{50}$ µM against MDA-MB-231 | IC$_{50}$ µM against HT-29 |
|---|---|---|---|---|---|---|
| 12 | 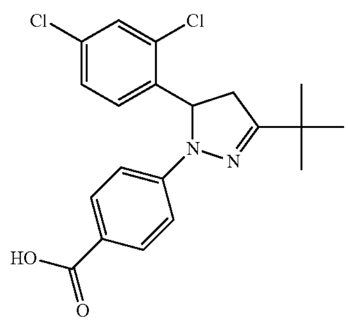 [SMILES: CC(C)(C)C1=NN(c2ccc(C(=O)O)cc2)C(c2ccc(Cl)cc2Cl)C1] | 3.7 | >100 | >100 | >50 | 29.8 |
| 13 | 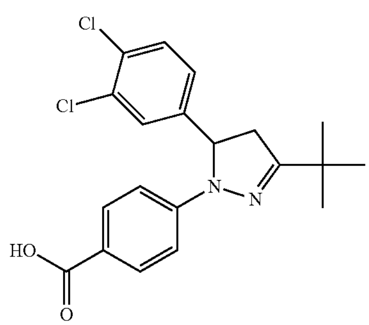 [SMILES: CC(C)(C)C1=NN(c2ccc(C(=O)O)cc2)C(c2ccc(Cl)c(Cl)c2)C1] | 5.5 | >100 | >100 | >50 | 25.7 |
| 14 | 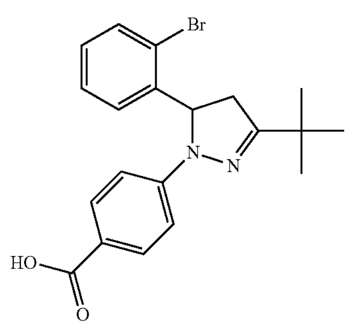 [SMILES: CC(C)(C)C1=NN(c2ccc(C(=O)O)cc2)C(c2ccccc2Br)C1] | 6.9 | >100 | >100 | >50 | 39.6 |
| 15 | 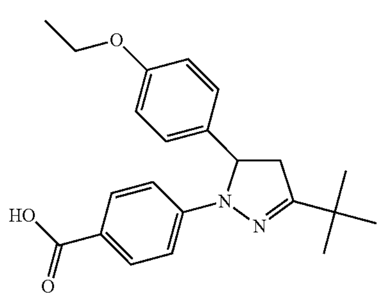 [SMILES: CCOc1ccc(C2CC(C(C)(C)C)=NN2c2ccc(C(=O)O)cc2)cc1] | 2.9 | >100 | >100 | >50 | 6.0 |

TABLE 1-continued

Inhibitory effect of the exemplified compounds against PDE5, COX1, COX2, and growth of the human breast MDA-MB-231 and colorectal HT-29 tumor cell lines.

| Compound ID | Structure | $IC_{50}$ μM against PDE5 | $IC_{50}$ μM against COX1 | $IC_{50}$ μM against COX2 | $IC_{50}$ μM against MDA-MB-231 | $IC_{50}$ μM against HT-29 |
|---|---|---|---|---|---|---|
| 16 | 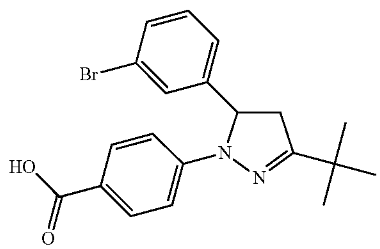 [SMILES: CC(C)(C)C1=NN(c2ccc(C(=O)O)cc2)C(c2cccc(Br)c2)C1] | 3.1 | >100 | >100 | >50 | 8.8 |
| 17 | 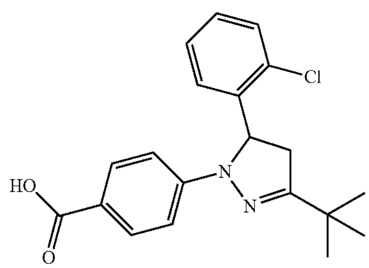 [SMILES: CC(C)(C)C1=NN(c2ccc(C(=O)O)cc2)C(c2ccccc2Cl)C1] | 1.9 | >100 | >100 | >50 | 20.8 |
| 18 | 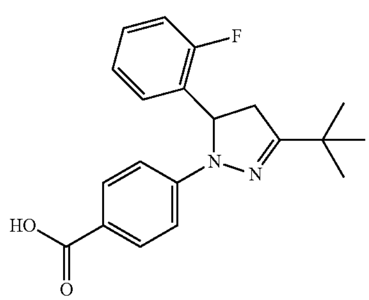 [SMILES: CC(C)(C)C1=NN(c2ccc(C(=O)O)cc2)C(c2ccccc2F)C1] | 3.3 | >100 | >100 | >50 | >50 |
| 19 | 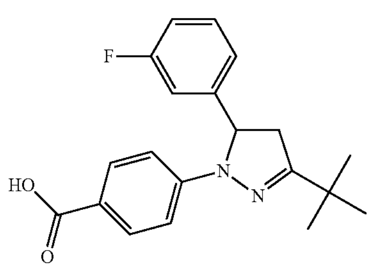 [SMILES: CC(C)(C)C1=NN(c2ccc(C(=O)O)cc2)C(c2cccc(F)c2)C1] | 2.7 | >100 | >100 | >50 | >50 |
| 20 | 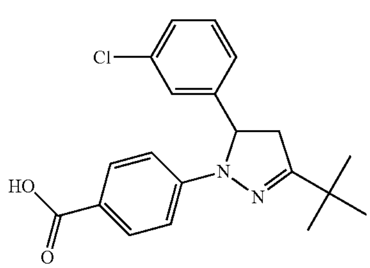 [SMILES: CC(C)(C)C1=NN(c2ccc(C(=O)O)cc2)C(c2cccc(Cl)c2)C1] | 2.0 | >100 | >100 | >50 | 22.0 |

TABLE 1-continued
Inhibitory effect of the exemplified compounds against PDE5, COX1, COX2, and growth of the human breast MDA-MB-231 and colorectal HT-29 tumor cell lines.
| Compound ID | Structure | IC$_{50}$ μM against PDE5 | IC$_{50}$ μM against COX1 | IC$_{50}$ μM against COX2 | IC$_{50}$ μM against MDA-MB-231 | IC$_{50}$ μM against HT-29 |
|---|---|---|---|---|---|---|
| 21 | 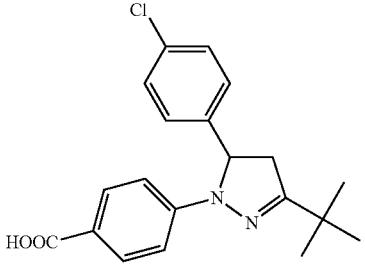 [SMILES: CC(C)(C)C1=NN(c2ccc(C(=O)O)cc2)C(c2ccc(Cl)cc2)C1] | 8.7 | >100 | >100 | >50 | >50 |
| 22 | 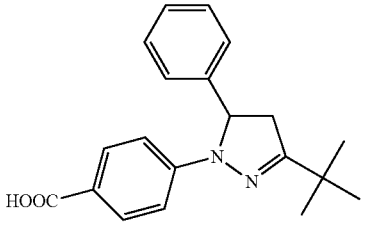 [SMILES: CC(C)(C)C1=NN(c2ccc(C(=O)O)cc2)C(c2ccccc2)C1] | 6.22 | >100 | >100 | >50 | >50 |
| 23 | 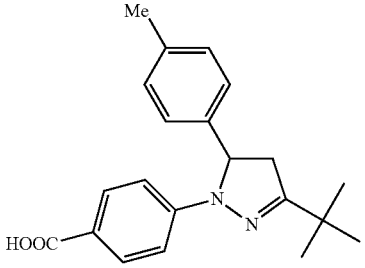 | 8.4 | >100 | >100 | >50 | >50 |
| 24 | 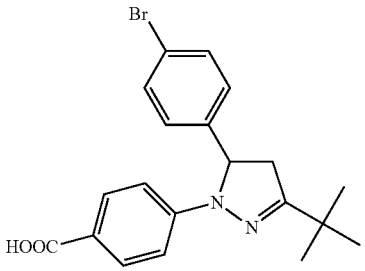 | 7.7 | >100 | >100 | >50 | >50 |
| 25 | 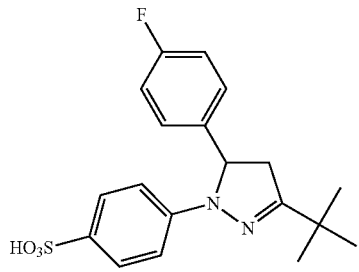 [SMILES: CC(C)(C)C1=NN(c2ccc(S(=O)(=O)O)cc2)C(c2ccc(F)cc2)C1] | 3.3 | >100 | >100 | >50 | >50 |

TABLE 1-continued

Inhibitory effect of the exemplified compounds against PDE5, COX1, COX2, and growth of the human breast MDA-MB-231 and colorectal HT-29 tumor cell lines.

| Compound ID | Structure | $IC_{50}$ µM against PDE5 | $IC_{50}$ µM against COX1 | $IC_{50}$ µM against COX2 | $IC_{50}$ µM against MDA-MB-231 | $IC_{50}$ µM against HT-29 |
|---|---|---|---|---|---|---|
| 26 | (structure) | 7.2 | >100 | >100 | >50 | >50 |
| 27 | (structure) | 3.1 | >100 | >100 | >50 | >50 |
| Celecoxib | (structure) celecoxib | 36.0 | 23.0 | 0.5 | >50 | 26.5 |

Compounds according to the present disclosure were tested for their in vitro ability to inhibit recombinant human PDE5, COX1 and COX2 enzymes at screening doses of 50, 100 and 100 µM respectively. The $IC_{50}$ was determined for compounds showing inhibition >50%.

The results of the testing are shown in Table 1. The partial saturation to the pyrazoline core resulted in complete loss of COX2 inhibition but retained or had improved PDE5 activity compared with celecoxib. Accordingly, the pyrazoline derivatives of celecoxib are preferred according to the present disclosure. The reduction of the double bond to the pyrazoline core results in a conformational change in the orientation of the aryl at position 5, which seems to be an important feature for the switch from COX2/COX1 inhibition to PDE5 inhibition.

Testing the synthesized compounds against the human breast cancer cell line, MDA-MB-231 and the colorectal cancer cell line, HT-29 showed that numerous compounds have appreciable tumor cell growth activity.

Compound 4-(3-tert-butyl-5-(2,4-dichlorophenyl)-4,5-dihydropyrazol-1-yl)benzoic acid (compound 12) was found to be a selective inhibitor for PDE5 relative to other cGMP degrading PDE isozymes as shown in Table 2.

TABLE 2

PDE5 isozyme selectivity of compound 12.

| PDE Isozyme | Substrate | $IC_{50}$ (µM) |
|---|---|---|
| PDE1A | cAMP | >50 |
|  | cGMP | >50 |
| PDE2A | cAMP | >50 |
|  | cGMP | >50 |

TABLE 2-continued

PDE5 isozyme selectivity of compound 12.

| PDE Isozyme | Substrate | IC$_{50}$ (µM) |
|---|---|---|
| PDE3A | cAMP | >50 |
|  | cGMP | >50 |
| PDE3B | cAMP | >50 |
|  | cGMP | >50 |
| PDE5A | cGMP | 3.7 |
| PDE9A | cGMP | >50 |
| PDE10 | cAMP | >50 |
|  | cGMP | >50 |
| PDE11 | cAMP | >50 |
|  | cGMP | >50 |

Compound 12 was also tested against human tumor cell lines of different origins and showed broad spectrum growth inhibitory activity including the adriamycin resistant cell line, ADR/NCl-RES. Thus, compound 12 is able to show broad spectrum tumor cell growth inhibitory activity independent of cyclooxygenase inhibition, whereas PDE5 may be the major contributor to such activity.

TABLE 3

Broad spectrum tumor cell growth inhibitory activity of compound 12.

| Origin | Cell line | IC$_{50}$ (µM) | Origin | Cell line | IC$_{50}$ (µM) |
|---|---|---|---|---|---|
| Hematopoietic | CCFR-CEM | 33.1 | Breast | T-47D | 63 |
|  | SR | 43 |  | MDA-MB-231 | 64.4 |
|  | HL-60 (TB) | 34.5 |  | MDA-MB-468 | 58.5 |
|  | K562 | 33.2 |  | BT-549 | 54.7 |
|  | RPMI-8226 | 23.2 |  | Hs578T | 48.9 |
|  | MOLT-4 | 20.7 |  | MCF-7 | 52.4 |
| Lung | NCI-H522 | 50.4 | Melanoma | UACC-62 | 42.3 |
|  | NCI-H460 | 42.9 |  | UACC-257 | 70 |
|  | NCI-H322M | 49.8 |  | LOX IMV1 | 50.5 |
|  | NCI-H23 | 40.6 |  | M14 | 62.9 |
|  | NCI-H226 | 56.4 |  | MALME-3M | 65.7 |
|  | A549 | 58 |  | MDA-MB-435 | 50.8 |
|  | EKVX | 57.2 |  | SK-MEL-2 | 44.5 |
|  | HOP-62 | 37.4 |  | SK-MEL-28 | 72.4 |
|  | HOP-92 | 52.8 |  |  |  |
| CNS | SNB-75 | 67.8 | Ovarian | OVCAR-5 | 59.4 |
|  | U251 | 33.3 |  | OVCAR-8 | 45.8 |
|  | SF-268 | 41.1 |  | OVCAR-4 | 54.9 |
|  | SNB-19 | 52.8 |  | OVCAR-3 | 37.8 |
|  | SF-539 | 52.9 |  | IGROV-1 | 59 |
|  | SF-295 | 45.8 |  | SKOV-3 | 87.4 |
| Colon | HCT-15 | 40.3 | Renal | ACHN | 55.3 |
|  | HCT-116 | 39 |  | UO-31 | 55.7 |
|  | HCC-2998 | 41.9 |  | CAKI-1 | 87 |
|  | KM12 | 34.7 |  | A498 | 33 |
|  | SW-620 | 51.8 |  | RXF-393 | 46.7 |
|  | COL0205 | 31.3 |  | SN12C | 50 |
|  | HT29 | 29.8 |  | 786-0 | 46.4 |
| Prostate | DU-145 | 59.6 |  | TK-10 | 74 |
|  | PC-3 | 55.1 | Other | NCI-ADR/RES | 57.2 |

EXPERIMENTAL 1.1 Chemistry

General Experimental Details
1. All starting materials and solvents were obtained from commercial suppliers, and were used without further purification.
2. Melting points were determined on Buchi B-540 Melting Point apparatus and are uncorrected.
3. $^{1}$H-NMR spectra were recorded at 500 MHz using a Bruker DRX-500 MHz spectrometer or at 300 MHz using Varian Mercury VX-300 MHz spectrometer. $^{13}$C-NMR spectra were recorded at 126 MHz using a Bruker DRX-126 MHz spectrometer. The solvents used were DMSO-d$_6$ or CDCl$_3$. Chemical shifts are given in parts per million (ppm), and all coupling constants (J) are given in Hz.
4. The purities of the tested compounds were determined by HPLC coupled with mass spectrometry and were all higher than 95% purity. Mass spectrometric analysis (HPLC-ESI-MS) was performed on a TSQ quantum (Thermo Electron Corporation) Instrument equipped with an ESI source and a triple quadrupole mass detector (Thermo Finnigan, San Jose, Calif.). The MS detection was carried out at a spray voltage of 4.2 kV, a nitrogen sheath gas pressure of 4.0105 Pa, an auxiliary gas pressure of 1.0105 Pa, a capillary temperature of 400° C., capillary voltage of 35 V, and source CID of 10 V. All samples were injected by autosampler (Surveyor, Thermo Finnigan) with an injection volume of 10 µL. A RP C18 NUCLEODUR 100-3 (125 mm3 mm) column (Macherey-Nagel) was used as stationary phase. The solvent system consisted of water containing 0.1% TFA (A) and 0.1% TFA in acetonitrile (B). HPLC-method: flow rate 400 µL/min. The percentage of B started at an initial of 5%, was increased up to 100% during 16 min, kept at 100% for 2 min, and flushed back to 5% in 2 min. All masses were reported as those of the parent ions.
5. FTIR spectra were recorded on Nicolet Avatar 380 spectrometer.
6. Column chromatography was performed using silica-gel 70-230 mesh.
7. Reaction progress was monitored by TLC using fluorescent pre-coated silica gel plates and detection of the components was made by short UV light (λ=254 nm).
8. Reactions were carried out under argon when it was needed.

1.2 Biology

1. Cell Culture
The human tumor cell lines were purchased from the American Type Culture Collection (Mansassas, Va.) and maintained in RPMI-1640+2.0 g/L glucose pH 7.4+5% FBS+4 mM glutamine (complete growth medium), incubated at 37° C. in 5% CO$_2$, and passaged at subconfluent density. The human fetal colon FHC cells were cultured in DMEM: F12 medium supplemented with 10% FBS, cholera toxin (10 ng/mL), 5 µg/ml transferrin, 5 µg/ml insulin, and 100 ng/ml hydrocortisone. The passage number was routinely limited to approximately 20 and morphology monitored with each passage, but no additional authentication of the cell lines was performed.
2. COX Activity
COX-1 and COX-2 activities were measured using purified ovine COX-1 and COX-2 with colorimetric assay kits obtained from Cayman Chemical Co. (Ann Arbor, Mich.). The activities of COX-1 and COX-2 were measured after the addition of arachidonic acid and incubation at 25° C. for 5 min by absorbance at 590 nm as specified by the manufacturer.
3. Growth Assays
Cells were plated in 96-well microtiter plates at a density of 5,000 cells per well and allowed to adhere overnight prior to treatment. Cells were treated with a 2-log concentration range of either SS or SBA and incubated for an additional 72 hours. For siRNA assays, cells were transfected in OptiMEM media with 0.5% SureFECT transfection reagent and 200 nmol/L of either negative control or PDE5 siRNA and incubated at 37°

C. for 24 h prior to treatment. At the end of the incubation period, relative cell viability was compared to vehicle controls using the Cell Titer Glo Assay (Promega, Madison Wis.), which measures viable cells based on ATP content, according to the manufacturer's specifications.

4. PDE Activity

PDE activity was measured using the IMAP fluorescence polarization assay (Molecular Devices) in which binding of hydrolyzed cyclic nucleotide substrate to immobilized metal coordination complexes increases fluorescence polarization (FP). Tetramethylrhodamine (TAMRA)-cGMP and fluorescein-cAMP were used as substrates, each at final concentration of 50 nmol/L. The PDE assay was done according to the manufacturer's specifications using either whole cell lysates or recombinant enzymes. FP was measured at excitation, emission wavelengths of either 530,590 nm for TAMRA-cGMP or 485,530 nm for fluorescein-cAMP using a Synergy4 (Biotek) microplate reader.

The following non-limiting examples further illustrate the disclosure

Example 1

4-(3-tert-Butyl-5-(4-methoxyphenyl)-4,5-dihydro-1H-pyrazol-1-yl)benzoic acid (1)

Yield: 30% white powder; m.p.: 208.9° C.; TLC: $R_f$=0.78 ($CH_2Cl_2$:$CH_3OH$, 5:1); $^1$H-NMR: δ 7.67 (d, J=9.01, Hz, 2H, ArH), 7.12 (d, J=8.73 Hz, 2H, ArH), 6.84-6.89 (m, 4H, ArH), 5.30 (dd, J=11.66, 5.00 Hz, 1H, H5), 3.70 (s, 3H, $OCH_3$), 3.55 (dd, J=17.70, 11.70 Hz, 1H, H4b), 2.72 (dd, J=17.70, 5.04 Hz, 1H, H4a), 1.18 (s, 9H, tBu); $^{13}$C-NMR: δ 27.86, 33.55, 42.56, 55.00, 61.66, 111.34, 114.33, 118.87, 126.78, 130.70, 134.11, 147.83, 158.45, 161.46, 167.26; IR ($cm^{-1}$): 2600-3200 (—OH), 1660 (—CO—); MS (ESI): 353.22 ($M^+$+1), 351.19 ($M^+$–1) $C_{21}H_{24}N_2O_3$; Purity (HPLC): 96.2%

Example 2

4-(3-tert-Butyl-5-(4-nitrophenyl)-4,5-dihydro-1H-pyrazol-1-yl)benzoic acid (2)

Yield: 35% yellow powder; m.p.: 245.2° C.; TLC: $R_f$=0.81 ($CH_2Cl_2$:$CH_3OH$, 5:1); $^1$H-NMR: δ 12.06 (brs, 1H, COOH), 8.06 (d, J=8.78, Hz, 2H, ArH), 7.54 (d, J=8.94 Hz, 2H, ArH), 7.32 (d, J=8.78 Hz, 2H, ArH), 6.70 (d, J=8.89 Hz, 2H, ArH), 5.42 (dd, J=11.88, 5.14 Hz, 1H, H5), 3.50 (dd, J=17.81, 11.93 Hz, 1H, H4b), 2.64 (dd, J=17.82, 5.15 Hz, 1H, H4a), 1.03 (s, 9H, tBu); $^{13}$C-NMR: δ 27.81, 33.58, 42.21, 61.56, 111.42, 119.51, 124.28, 127.06, 130.86, 146.85, 147.52, 149.64, 161.60, 167.16; IR ($cm^{-1}$): 2600-3200 (—OH), 1678 (—CO—), 2966 (C—H); MS (ESI): 366.22 ($M^+$–1) $C_{20}H_{21}N_3O_4$; Purity (HPLC): 99.81%

Example 3

4-(3-tert-Butyl-5-(3-nitrophenyl)-4,5-dihydro-1H-pyrazol-1-yl)benzoic acid (3)

Yield: 50%; Yellow powder; m.p.: 235.4° C.; TLC: $R_f$=0.36 ($CH_2Cl_2$:$CH_3OH$, 100:2); $^1$H-NMR: δ 8.11 (d, J=9.5 Hz, 2H), 7.67 (dd, J=16.8, 7.5 Hz, 4H), 6.89 (d, J=7.9 Hz, 2H), 5.60 (dd, J=11.52, 4.69 Hz, 1H), 3.65 (dd, J=17.9, 11.7 Hz, 1H), 2.84 (dd, J=17.99, 4.40 Hz, 1H), 1.19 (s, 9H); IR ($cm^{-1}$): 2800-3200 (—OH), 1660 (—CO—); MS (ESI): 367.65 ($M^+$) $C_{20}H_{21}N_3O_4$; Purity (HPLC): 97.6%.

Example 4

4-(3-tert-Butyl-5-(2,4-dimethoxyphenyl)-4,5-dihydro-1H-pyrazol-1-yl)benzoic acid (4)

Yield: 58% Yellowish green powder; m.p.: 213.5° C.; TLC: $R_f$=0.35 ($CH_2Cl_2$:$CH_3OH$, 100:2); $^1$H-NMR: δ 7.67 (d, J=8.7 Hz, 2H), 6.76 (t, J=9.0 Hz, 3H), 6.61 (s, 1H), 6.41 (d, J=8.4 Hz, 1H), 5.39 (dd, J=11.8, 4.8 Hz, 1H), 3.86 (s, 3H), 3.72 (s, 3H), 3.53 (dd, J=17.7, 11.9 Hz, 1H), 2.64 (dd, J=17.5, 4.9 Hz, 1H), 1.17 (s, 9H); IR ($cm^{-1}$): 2800-3200 (—OH), 1660 (—CO—); MS (ESI): 382.60 ($M^+$) $C_{22}H_{26}N_2O_4$; Purity (HPLC): 100%.

Example 5

4-(3-tert-Butyl-5-(4-hydroxyphenyl)-4,5-dihydro-1H-pyrazol-1-yl)benzoic acid (5)

Yield: 65% white powder; m.p.: 259.1° C.; TLC: $R_f$=0.14 ($CH_2Cl_2$:$CH_3OH$, 100:2); $^1$H-NMR: (δ) 7.83 (d, J=9 Hz, 2H), 7.06 (d, J=8.9 Hz, 2H), 6.9 (d, J=5.2 Hz, 2H), 6.77 (d, J=3.4 Hz, 2H), 5.09 (dd, J=11.7, 5.1 Hz, 1H), 3.48 (dd, J=17.2, 11.7 Hz, 1H), 2.78 (dd, J=17.2, 5.09 Hz, 1H), 1.22 (s, 9H); IR ($cm^{-1}$): 3359.2 (—OH), 2800-3200 (—OH), 1648.7 (—CO—); MS (ESI): 338.16 ($M^+$) $C_{20}H_{22}N_2O_3$; Purity (HPLC): 96%.

Example 6

3-(3-tert-Butyl-5-(4-chlorophenyl)-4,5-dihydro-4H-pyrazol-1-yl)benzoic acid (6)

Yield: 61% Faint yellow powder; m.p. 245° C.; TLC: $R_f$=0.38 ($CH_2Cl_2$:$CH_3OH$, 100:2); $^1$H-NMR: δ 7.70-7.67 (m, 2H), 7.41-7.38 (m, 2H), 7.23-7.20 (m, 2H), 6.86-6.83 (m, 2H), 5.40 (dd, J=11.7, 5.0 Hz, 1H), 3.58 (dd, J=17.8, 11.8 Hz, 1H), 2.74 (dd, J=17.8, 5.0 Hz, 1H), 1.18 (s, 9H); $^{13}$C-NMR: δ 167.22, 161.52, 147.63, 141.09, 131.91, 130.79, 128.98, 127.54, 119.18, 111.35, 61.45, 42.36, 33.53, 27.80; IR ($cm^{-1}$): 2800-3200 (—OH), 1662.5 (—CO—); MS (ESI): 356.71 ($M^+$), 358.58 ($M^+$+2); $C_{20}H_{21}ClN_2O_2$; Purity (HPLC): 100%.

Example 7

4-(5-(4-Methoxyphenyl)-3-phenyl-4,5-dihydro-1H-pyrazol-1-yl)benzoic acid (7)

Yield: 60% Yellow powder; m.p.: 225.8° C.; TLC: $R_f$=0.4 ($CH_2Cl_2$:$CH_3OH$, 100:2); $^1$H-NMR: δ 7.80-7.77 (m, 2H), 7.73 (d, J=9.0 Hz, 2H), 7.47-7.38 (m, 3H), 7.20-7.16 (m, 2H), 7.06-7.03 (m, 2H), 6.91-6.87 (m, 2H), 5.57 (dd, J=12.0, 5.1 Hz, 1H), 3.93 (dd, J=17.6, 12.0 Hz, 1H), 3.70 (s, 3H), 3.15 (dd, J=17.6, 5.1 Hz, 1H); $^{13}$C-NMR: δ 167.20, 158.57, 149.62, 146.94, 133.70, 131.84, 130.75, 129.23, 128.69, 126.95, 126.02, 119.85, 114.41, 111.98, 61.88, 55.01, 42.99; IR ($cm^{-1}$): 2800-3200 (—OH), 1669.3 (—CO—); MS (ESI): 372.67 ($M^+$) $C_{23}H_{20}N_2O_3$; Purity (HPLC): 100%.

Example 8

4-(3-(2-Methoxyphenyl)-5-(4-methoxyphenyl)-4,5-dihydro-1H-pyrazol-1-yl)benzoic acid (8)

Yield: 56% Dark yellow powder; m.p.: 242.8° C.; TLC: $R_f$=0.34 ($CH_2Cl_2$:$CH_3OH$, 100:2); $^1$H-NMR: δ 7.93 (dd, J=7.8, 1.7 Hz, 1H), 7.72 (d, J=9.1 Hz, 2H), 7.41-7.36 (m, 1H), 7.19-7.15 (m, 2H), 7.10-7.07 (m, 1H), 7.03-6.99 (m, 3H), 6.91-6.87 (m, 2H), 5.49 (dd, J=11.9, 5.1 Hz, 1H), 3.99 (dd, J=18.2, 12.0 Hz, 1H), 3.79 (s, 3H), 3.70 (s, 3H), 3.20 (dd, J=18.2, 5.1 Hz, 1H); $^{13}$C-NMR: δ 167.22, 158.51, 157.47, 148.88, 147.07, 133.89, 130.74, 128.31, 126.85, 120.74, 120.67, 119.60, 114.38, 112.35, 111.89, 64.88, 61.77, 55.63, 54.99, 46.36; IR (cm$^{-1}$): 2800-3200 (—OH), 1660.4 (—CO—); MS (ESI): 402.63 (M$^+$) $C_{24}H_{22}N_2O_4$; Purity (HPLC): 92.17%.

Example 9

4-(3-(3-Methoxyphenyl)-5-(4-methoxyphenyl)-4,5-dihydro-1H-pyrazol-1-yl)benzoic acid (9)

Yield: 30% Yellow powder; m.p.: 142.2° C.; TLC: $R_f$=0.38 (CH$_2$Cl$_2$:CH$_3$OH, 100:2); $^1$H-NMR: δ 7.72 (d, J=9.1 Hz, 2H), 7.40-7.36 (m, 3H), 7.20-1.18 (m, 2H), 7.10-6.87 (m, 5H), 5.60 (dd, J=11.9, 5.1 Hz, 1H), 3.99 (dd, J=18.2, 12.0 Hz, 1H), 3.90 (s, 3H), 3.70 (s, 3H), 3.20 (dd, J=18.2, 5.1 Hz, 1H); IR (cm$^{-1}$): 2800-3200 (—OH), 1660 (—CO—); MS (ESI): 402.63 (M$^+$) $C_{24}H_{22}N_2O_4$; Purity (HPLC): 98.67%.

Example 10

4-(3-(3,4-Dimethoxyphenyl)-5-(4-methoxyphenyl)-4,5-dihydro-1H-pyrazol-1-yl)benzoic acid (10)

Yield: 62% Yellow powder; m.p.: 140.6° C.; TLC: $R_f$=0.3 (CH$_2$Cl$_2$:CH$_3$OH, 100:2); $^1$H-NMR: δ 7.72 (d, J=9.1 Hz, 2H), 7.42 (d, J=2.0 Hz, 1H), 7.23 (dd, J=8.3, 2.0 Hz, 1H), 7.19-7.15 (m, 2H), 7.04-6.98 (m, 3H), 6.91-6.87 (m, 2H), 5.53 (dd, J=11.9, 5.0 Hz, 1H), 3.89 (dd, J=17.5, 12.0 Hz, 1H), 3.84 (s, 3H), 3.79 (s, 3H), 3.70 (s, 3H), 3.14 (dd, J=17.5, 5.0 Hz, 1H); $^{13}$C-NMR: δ 167.24, 158.54, 150.12, 149.82, 148.83, 147.05, 133.82, 130.73, 126.90, 124.55, 119.61, 119.41, 114.39, 111.77, 111.48, 108.69, 64.88, 61.73, 55.55, 55.01, 43.21; IR (cm$^{-1}$): 2800-3200 (—OH), 1665.1 (—CO—); MS (ESI): 432.50 (M$^+$) $C_{25}H_{24}N_2O_5$; Purity (HPLC): 99.2%.

Example 11

4-(5-(4-Methoxyphenyl)-3-phenyl-4,5-dihydro-1H-pyrazol-1-yl)benzenesulfonamide (11)

Yield: 57% Faint yellow powder; m.p.: 110.7° C.; TLC: $R_f$=0.58 (CH$_2$Cl$_2$:CH$_3$OH, 100:2); $^1$H-NMR: δ 7.81-7.77 (m, 2H), 7.61-7.57 (m, 2H), 7.47-7.38 (m, 3H), 7.20-7.16 (m, 2H), 7.11-7.07 (m, 2H), 6.92-6.88 (m, 2H), 5.58 (dd, J=12.0, 5.1 Hz, 1H), 3.94 (dd, J=17.6, 12.0 Hz, 1H), 3.70 (s, 3H), 3.16 (dd, J=17.6, 5.2 Hz, 1H); $^{13}$C-NMR: δ 158.58, 149.57, 145.86, 133.47, 132.97, 131.82, 129.24, 128.69, 127.06, 126.99, 126.01, 114.41, 112.01, 61.86, 55.01, 42.96; IR (cm$^{-1}$): 3314.5, 3264.1 (—NH$_2$); MS (ESI): 407.62 (M$^+$) $C_{22}H_{21}N_3O_3S$; Purity (HPLC): 100%.

Example 12

4-(3-(tert-Butyl)-5-(2,4-dichlorophenyl)-4,5-dihydro-1H-pyrazol-1-yl)benzoic acid (12)

Yield: 40%, off-white powder; m.p.: 213.4° C.; TLC: $R_f$=0.38; $^1$H-NMR: δ 11.82 (s, 1H, COOH), 7.75-7.68 (m, 2H, ArH), 7.39-7.32 (mm, 1H, ArH), 6.96 (d, J=8.42 Hz, 2H, ArH), 6.77 (d, J=8.10 Hz, 2H, ArH), 5.54 (dd, J=11.84, 5.09 Hz, 1H, H5), 3.70 (dd, J=17.78, 11.89 Hz, 1H, H4b), 2.75 (dd, J=12.75, 5.09 Hz, 1H, H4a), 1.17 (s, 9H, tBu); IR (cm$^{-1}$): 1665 (—C=O), 2400-3200 (—OH); MS (EI): 390 (M$^+$), 392 (M$^+$+2), 394 (M$^+$+4) $C_{20}H_{20}Cl_2N_2O_2$; Purity (HPLC): 98.5%.

Example 13

4-(3-(tert-Butyl)-5-(3,4-dichlorophenyl)-4,5-dihydro-1H-pyrazol-1-yl)benzoic acid (13)

Yield: 90%, greenish yellow powder; m.p: 216.7° C.; TLC: $R_f$=0.38 (CH$_2$Cl$_2$:CH$_3$OH, 5:1); $^1$H-NMR: δ 11.99 (s, 1H, COOH), 7.68-7.59 (m, 1H, ArH), 7.49 (d, J=2.05 Hz, 1H, ArH), 7.14 (d, J=2.06 Hz, 1H, ArH), 7.11 (d, J=2.06 Hz, 2H, ArH), 6.87-6.84 (m, 2H, ArH), 5.42 (dd, J=11.65, 5.02 Hz, 1H, H5), 3.59 (dd, J=17.86, 11.77 Hz, 1H, H4b), 2.80 (dd, J=17.87, 5.04 Hz, 1H, H4a), 1.18 (s, 9H, tBu); IR (cm$^{-1}$): 1672 (—C=O), 2300-3100 (—OH); MS (EI): 390 (M$^+$), 392 (M$^+$+2), 394 (M$^+$+4) $C_{20}H_{20}Cl_2N_2O_2$; Purity (HPLC): 99.1%.

Example 14

4-(5-(2-Bromophenyl)-3-(tert-butyl)-4,5-dihydro-1H-pyrazol-1-yl)benzoic acid (14)

Yield: 74%, yellow powder; imp: 200.2° C.; TLC: $R_f$=0.36 (CH$_2$Cl$_2$:CH$_3$OH, 5:1); $^1$H-NMR: δ 12.00 (s, 1H, COOH), 7.43 (d, J=4.02 Hz, 1H, ArH), 7.65-7.73 (m, 2H, ArH), 7.29 (d, J=7.53 Hz, 1H, ArH), 7.17-7.15 (m, 2H, ArH), 6.89-6.82 (m, 2H, ArH), 5.39 (dd, J=11.37, 5.12 Hz, 1H, H5), 3.59 (dd, J=17.18, 11.79 Hz, 1H, H4b), 2.78 (dd, J=17.58, 4.59 Hz 1H, H4a), 1.18 (s, 9H, tBu); IR (cm$^{-1}$): 1665 (—C=O), 2500-3100 (—OH); MS (EI): 400 (M$^+$), 402 (M$^+$+2) $C_{20}H_{21}BrN_2O_2$; Purity (HPLC): 97.1%.

Example 15

4-(3-(tert-Butyl)-5-(4-ethoxyphenyl)-4,5-dihydro-1H-pyrazol-1-yl)benzoic acid (15)

Yield: 50%, beige powder; m.p: 159.8° C.; TLC: $R_f$=0.4 (CH$_2$Cl$_2$:CH$_3$OH, 5:1); $^1$H-NMR: δ 11.82 (s, 1H, COOH). 7.67-7.64 (m, 2H, ArH), 7.11-7.08 (m, 2H, ArH), 6.88-6.83 (m, 4H, ArH), 5.30 (dd, J=11.57, 4.97 Hz, 1H, H5), 3.97 (q, J=6.96 Hz, 2H, OCH2), 3.56 (dd, J=17.71, 11.68 Hz, 1H, H4b), 2.72 (dd, J=17.75, 5.01 Hz, 1H, H4a), 1.29 (t, J=6.96 Hz, 3H, CH3), 1.19 (s, 9H, tBu); IR (cm$^{-1}$): 1658 (—C=O), 2700-3200 (—OH); MS (EI): 366 (M$^+$) $C_{22}H_{26}N_2O_3$; Purity (HPLC): 98.5%.

Example 16

4-(5-(3-Bromophenyl)-3-(tert-butyl)-4,5-dihydro-1H-pyrazol-1-yl)benzoic acid (16)

Yield: 43%, yellow powder; m.p: 215.5° C.; TLC: $R_f$=0.43 (CH$_2$Cl$_2$:CH$_3$OH, 5:1); $^1$H-NMR: δ 11.99 (s, 1H, COOH), 7.71 (d, J=1.26 Hz, 2H, ArH), 7.31 (d, J=1.35 Hz, 1H, ArH), 7.25 (d, J=1.89 Hz, 1H, ArH), 7.22 (d, J=1.81 Hz, 1H, ArH), 7.20-7.19 (m, 1H, ArH), 6.94 (d, J=7.35 Hz, 2H, ArH), 6.77-6.72 (m, 1H, ArH), 5.50 (dd, J=11.79, 5.07 1H, H5), 3.71 (dd, J=17.77, 11.85 Hz, 1H, H4b), 2.70 (dd J=17.81, 5.13 Hz, 1H, H4a), 1.18 (s, 9H, tBu); IR (cm$^{-1}$): 1672 (—C=O), 2700-

3200 (—OH); MS (EI): 400 (M$^+$), 402 (M$^+$+2) C$_{20}$H$_{21}$BrN$_2$O$_2$; Purity (HPLC): 99.5%.

Example 17

4-(3-(tert-Butyl)-5-(2-chlorophenyl)-4,5-dihydro-1H-pyrazol-1-yl)benzoic acid (17)

Yield: 47%, orange crystals; m.p: 229.2° C.; TLC: R$_f$=0.45 (CH$_2$Cl$_2$:CH$_3$OH, 5:1); $^1$H-NMR: δ 11.66 (s, 1H, COOH), 7.71 (d, J=8.95 Hz, 1H, ArH), 7.51 (d, J=1.41 Hz, 1H, ArH), 7.54 (d, J=1.71 Hz, 1H, ArH), 6.99 (d, J=1.95 Hz, 1H, ArH), 6.97 (d, J=2.03 Hz, 2H, ArH), 6.77 (d, J=8.91 Hz, 2H, ArH), 5.56 (dd, J=11.87, 5.22 Hz, 1H, H5), 3.70 (dd, J=17.78, 11.88 Hz, 1H, H4b), 2.74 (dd, J=17.55, 5.66 Hz, 1H, H4a), 1.17 (s, 9H, tBu); IR (cm$^{-1}$): 1666 (—C═O), 2700-3200 (—OH); MS (EI): 356 (M$^+$), 358 (M$^+$+2); C$_{20}$H$_{21}$ClN$_2$O$_2$; Purity (HPLC): 96.6%.

Example 18

4-(3-(tert-Butyl)-5-(2-fluorophenyl)-4,5-dihydro-1H-pyrazol-1-yl)benzoic acid (18)

Yield: 70%, beige powder; m.p: 224.6° C.; TLC: R$_f$=0.52 (CH$_2$Cl$_2$:CH$_3$OH, 5:1); $^1$H-NMR: δ 12.12 (s, 1H, COOH), 7.09 (d, J=1.87 Hz, 1H, ArH), 7.06 (d, J=1.75 Hz, 1H, ArH), 7.72-7.67 (m, 2H, ArH), 7.24 (d, J=1.08 Hz, 1H, ArH), 7.13 (d, J=1.06 Hz, 1H, ArH), 6.84 (d, J=8.88 Hz, 2H, ArH), 5.54 (dd, J=11.89, 4.99 Hz, 1H, H5), 3.64 (dd, J=17.72, 11.84 Hz, 1H, H4b), 2.82 (dd, J=17.81, 4.93 Hz, 1H, H4a), 1.19 (s, 9H, tBu); IR (cm$^{-1}$): 1672 (—C═O), 2600-3200 (—OH); MS (EI): 340 (M$^+$); C$_{20}$H$_{21}$FN$_2$O$_2$; Purity (HPLC): 97.5%.

Example 19

4-(3-(tert-Butyl)-5-(3-fluorophenyl)-4,5-dihydro-1H-pyrazol-1-yl)benzoic acid (19)

Yield: 53%, beige powder; m.p: 218.5° C.; TLC: R$_f$=0.62 (CH$_2$Cl$_2$:CH$_3$OH, 5:1); $^1$H-NMR: δ 11.76 (s, 1H, COOH); 7.73-7.64 (m, 2H, ArH), 7.40 (d, J=1.79 Hz, 1H, ArH), 7.37 (d, J=2.00 Hz, 1H, ArH), 7.08 (d, J=1.97 Hz, 1H, ArH), 6.90-6.80 (m, 3H, ArH), 5.40 (dd, J=11.77, 5.16 Hz, 1H, H5), 3.60 (dd, J=17.81, 11.78 Hz, 1H, H4b), 2.78 (dd, J=17.79, 5.18 Hz, 1H, H4a), 1.19 (s, 9H, tBu); IR (cm$^{-1}$): 1616 (—C═O), 2700-3200 (—OH); MS (EI): 340 (M$^+$) C$_{20}$H$_{21}$FN$_2$O$_2$; Purity (HPLC): 97.5%.

Example 20

4-(3-(tert-Butyl)-5-(2-ethoxyphenyl)-4,5-dihydro-1H-pyrazol-1-yl)benzoic acid (20)

Yield: 63%, greenish yellow powder; m.p: 213.4° C.; TLC: R$_f$=0.52 (CH$_2$Cl$_2$:CH$_3$OH, 5:1); $^1$H-NMR: δ 12.00 (s, 1H, COOH), 7.19 (d, J=2.30 Hz, 1H, ArH), 7.67 (d, J=8.85 Hz, 2H, ArH), 6.85-6.76 (m, 1H, ArH), 6.85 (d, J=2.06 Hz, 2H, ArH), 6.78 (d, J=8.86 Hz, 2H, ArH), 5.48 (dd, J=11.89, 5.40 Hz, 1H, H5), 4.19-4.08 (m, 2HOCH3), 3.59 (dd, J=17.76, 11.89 Hz, 1H, H4b), 2.68 (dd, J=17.75, 5.41 Hz, 1H, H4a), 1.39 (t, J=6.94, 3H, CH2), 1.18 (s, 9H, tBu); IR (cm$^{-1}$): 1665 (—C═O), 2700-3200 (—OH); MS (EI): 366 (M$^+$) C$_{22}$H$_{26}$N$_2$O$_3$; Purity (HPLC): 95.5%.

Example 21

4-(3-tert-Butyl-5-(4-chlorophenyl)-4,5-dihydro-1H-pyrazol-1-yl)benzoic acid (21)

Yield: 41% white crystals; m.p.: 208.5° C.; TLC: R$_f$=0.81 (CH$_2$Cl$_2$:CH$_3$OH, 5:1); $^1$H-NMR: δ 12.26 (brs, 1H, COOH), 7.74 (d, J=8.91 Hz, 2H, ArH), 7.45 (d, J=8.46, Hz, 2H, ArH), 7.27 (d, J=8.48 Hz, 2H, ArH), 6.90 (d, J=8.87 Hz, 2H, ArH), 5.45 (dd, J=11.73, 4.97 Hz, 1H, H5), 3.64 (dd, J=17.75, 11.80 Hz, 1H, H4b), 180 (dd, J=17.75, 5.03 Hz, 1H, H4a), δ 1.2 (s, 9H, tBu); $^{13}$C-NMR: 627.82, 33.54, 42.36, 61.45, 111.36, 119.20, 127.54, 128.97, 130.78, 131.90, 141.09, 147.63, 161.52, 167.21; IR (cm$^{-1}$): 2600-3200 (–OH), 1665 (—CO—); MS (ESI): 357.17 (M$^+$), 355.05 (M$^+$-2) C$_{20}$H$_{21}$ClN$_2$O$_2$; Purity (HPLC): 100%

Example 22

4-(3-tert-Butyl-5-phenyl-4,5-dihydro-1H-pyrazol-1-yl)benzoic acid (22)

Yield: 38% white powder; m.p.: 233.3° C.; TLC: R$_f$=0.77 (CH$_2$Cl$_2$:CH$_3$OH, 5:1); $^1$H-NMR: δ 12.00 (brs, 1H, COOH), 7.55 (d, J=8.92 Hz, 2H), 7.21 (t, J=7.54, 7.54 Hz, 2H), 7.13 (t, J=7.37, 7.37 Hz, 1H), 7.10-7.07 (m, 2H), 6.74 (d, J=8.87 Hz, 2H), 5.24 (dd, J=11.75, 5.12 Hz, 1H, H5), 3.48 (dd, J=17.72, 11.79 Hz, 1H, H4b), 2.63 (dd, J=17.75, 5.15 Hz, 1H, H4a), 1.06 (s, 9H, tBu); $^{13}$C-NMR: δ 27.85, 33.54, 42.57, 62.17, 111.30, 118.96, 125.54, 127.38, 128.98, 130.73, 142.22, 147.81, 161.46, 167.23; IR (cm): 2500-3200 (—OH), 1659 (—CO—); MS (ESI): 323.23 (M$^+$+1), 321.26 (M$^+$−1) C$_{20}$H$_{22}$N$_2$O$_2$; Purity (HPLC): 98.84%

Example 23

4-(3-tert-Butyl-5-p-tolyl-4,5-dihydro-1H-pyrazol-1-yl)benzoic acid (23)

Yield: 35% yellow powder; m.p.: 194.6° C.; TLC: R$_f$=0.8 (CH$_2$Cl$_2$:CH$_3$OH, 5:1); $^1$H-NMR: δ 12.16 (brs, 1H, COOH), 7.67 (d, J=8.53 Hz, 2H, ArH), 7.14 (d, J=7.91, Hz, 2H, ArH), 7.09 (d, J=7.9 Hz, 2H, ArH), 6.86 (d, J=8.64 Hz, 2H, ArH), 5.32 (dd, J=11.66, 4.99 Hz, 1H, H5), 3.58 (dd, J=17.68, 11.82 Hz, 1H, H4b), 2.73 (dd, J=17.98, 4.76 Hz, 1H, H4a), 2.25 (s, 3H, CH3), 1.19 (s, 9H, tBu); $^{13}$C-NMR: δ 20.59, 27.83, 33.54, 42.53, 55.00, 61.93, 111.29, 118.87, 125.46, 129.52, 130.70, 136.53, 147.80, 161.44, 167.25; IR (cm$^{-1}$): 2500-3200 (—OH), 1666 (—CO—); MS (ESI): 337.22 (M$^+$+1), 335.24 (M$^+$−1) C$_{21}$H$_{24}$N$_2$O$_2$; Purity (HPLC): 98.81%.

Example 24

4-(5-(4-Bromophenyl)-3-tert-butyl-4,5-dihydro-1H-pyrazol-1-yl)benzoic acid (24)

Yield: 32% yellow crystals; m.p.: 222.2° C.; TLC: R$_f$ 0.77 (CH$_2$Cl$_2$:CH$_3$OH, 5:1); $^1$H-NMR: δ 12.19 (brs, 1H, COOH), 7.69 (d, J=8.98 Hz, 2H, ArH), 7.54 (d, J=8.46, Hz, 2H, ArH), 7.16 (d, J=8.47 Hz, 2H, ArH), 6.85 (d, J=8.90 Hz, 2H, ArH), 5.39 (dd, J=11.75, 4.99 Hz, 1H, H5), 3.60 (dd, J=17.76, 11.78 Hz, 1H, H4b), 2.76 (dd, J=17.75, 5.01 Hz, 1H, H4a), 1.19 (s, 9H, tBu); $^{13}$C-NMR: δ 27.82, 33.54, 42.30, 61.50, 111.35, 119.20, 120.42, 127.90, 130.79, 131.84, 141.51, 147.62, 161.53, 167.20; IR (cm$^{-1}$): 2540-3200 (—OH), 1664 (—CO—); MS (ESI): 398.99 (M$^+$−2), 401.04 (M$^+$) C$_{20}$H$_2$, BrN$_2$O$_2$; Purity (HPLC): 98.62%.

Example 25

4-(3-tert-Butyl-5-(4-fluorophenyl)-4,5-dihydro-1H-pyrazol-1-yl)benzenesulfonic acid (25)

Yield: 25% yellow crystals; m.p.: 92.9° C.; TLC: R$_f$=0.35 (CH$_2$Cl$_2$:CH$_3$OH, 5:1); $^1$H-NMR: δ 7.65-7.73 (m, 4H, ArH), 7.6 (d, J=8.57 Hz, 2H, ArH), 6.75 (d, J=5.59 Hz, 2H, ArH), 5.28 (dd, J=11.65, 5.76 Hz, 1H, H5), 3.53 (dd, J=17.49, 11.69 Hz, 1H, H4b), 2.69 (dd, J=17.51, 5.81 Hz, 1H, H4a), 1.17 (s, 9H, tBu); $^{13}$C-NMR: δ 27.91, 33.43, 62.09, 67.39, 111.19, 115.51, 115.68, 124.06, 127.59, 128.63, 131.70, 146.82, 161.73; IR (cm$^{-1}$): 3000-3300 (—OH), 1040, 1180 (—SO2); MS (ESI): 375.1 (M$^+$+1) C$_{20}$H$_{21}$FN$_2$O$_2$; Purity (HPLC): 93.20%.

Example 26

4-(3-tert-Butyl-5-(4-chlorophenyl)-4,5-dihydro-1H-pyrazol-1-yl)benzenesulfonic acid (26)

Yield: 27% white crystals; m.p.: 92.5° C.; TLC: R$_f$=0.36 (CH$_2$Cl$_2$:CH$_3$OH, 5:1); $^1$H-NMR: δ 7.34 (d, J=8.84 Hz, 2H, ArH), 7.37 (d, J=8.53 Hz, 2H, ArH), 7.22 (d, J=8.48 Hz, 2H), 6.74 (d, J=8.83 Hz, 2H), 5.28 (dd, J=11.69, 5.80 Hz, 1H, H5), 3.54 (dd, J=17.53, 11.74 Hz, 1H, H4b), 2.69 (dd, J=17.52, 5.83 Hz, 1H, H4a), 1.2 (s, 9H, tBu); $^{13}$C-NMR: δ 27.91, 30.29, 42.28, 62.14, 111.17, 126.42, 127.70, 128.83, 131.70, 137.93, 141.40, 144.93, 159.57; IR (cm$^{-1}$): 3000-3600 (—OH), 1022, 1169 (—SO2-); MS (ESI): 391.14 (M$^+$−2), 393.03 (M$^+$) C$_{20}$H$_{21}$ClN$_2$O$_2$; Purity (HPLC): 100%.

Example 27

4-(3-(4-Fluorophenyl)-5-(4-methoxyphenyl)-4,5-dihydropyrazol-1-yl)benzoic acid (27)

Yield: 41% white crystals; m.p.: 218.5° C.; TLC: R$_f$=0.61 (CH$_2$Cl$_2$:CH$_3$OH, 5:1); $^1$H-NMR: δ 12.16 (brs, 1H, COOH), 7.74-7.60 (m, 4H, ArH), 7.50-7.40 (m, 4H, ArH), 7.27 (d, J=8.40 Hz, 2H, ArH), 6.95 (d, J=8.87 Hz, 2H, ArH), 5.40 (dd, J=11.73, 4.97 Hz, 1H, H5), 3.60 (dd, J=17.75, 11.80 Hz, 1H, H4b), 3.72 (S, 3H, —CH$_3$), 2.80 (dd, J=17.75, 5.03 Hz, 1H, H4a); $^{13}$C-NMR: δ 27.82, 33.54, 42.36, 61.45, 111.36, 119.20, 127.54, 128.97, 130.78, 131.90, 141.09, 147.63, 161.52, 167.21; IR (cm$^{-1}$): 2600-3200 (—OH), 1665 (—CO—); MS (ESI): 390.32 (M$^+$) C$_{23}$H$_{19}$FN$_2$O$_3$; Purity (HPLC): 99.0%.

In keeping with the present disclosure, the derivatives of celecoxib can be used alone or in appropriate association, and also may be used in combination with pharmaceutically acceptable carriers and other pharmaceutically active compounds such as various cancer treatment drugs including NSAIDs and/or along with radiation. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The derivatives of celecoxib alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

The present disclosure further provides a method of treating cancer in a mammal, especially humans. The method comprises administering an effective treatment amount of a derivative of celecoxib disclosed above to the mammal.

As regards these applications, the present method includes the administration to an animal, particularly a mammal, and more particularly a human, of a therapeutically effective amount of the compound effective in the inhibition of neoplasia and tumor growth and treating malignant disease including metastases, especially colorectal and breast cancer. The method also includes the administration of a therapeutically effect amount of the compound for the treatment of precancerous lesions such as adenomatous polyps of the colon and other dysplastic lesions of the skin (actinic keratosis), bladder, cervix, esophagus, oral cavity, lung, prostate and breast that are sometimes referred to as intraepithelial neoplasia.

The disclosed compounds and compositions can be administered to treat a number of cancers, including leukemias and lymphomas such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The present disclosure also relates to treating certain chronic inflammatory conditions which NSAIDs have shown benefit, but may be contraindicated due to cyclooxygenase inhibition (i.e.—inflammatory bowel disease) or do not appear to require cyclooxygenase inhibition for efficacy such as certain neurodegenerative diseases, including Alzheimer's disease. Still there are additional disease indications that benefit from treatment with NSAIDs, which can also be treated or prevented with compounds described in the present disclosure.

The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to affect the desired response. The preferred dosage is the amount which results in maximum inhibition of cancer, without unmanageable side effects.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method disclosed comprises further administering of chemotherapeutic agent other than the derivatives of the present invention. Any suitable chemotherapeutic agent can be employed for this purpose. The chemotherapeutic agent is typically selected from the group consisting of alkylating agents, antimetabolites, natural products, anti-inflammatory agents, hormonal agents, molecular targeted drugs, anti-angiogenic drugs, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside fluorouracil, gemcitabine, mercaptopurine, methotrexate, thioguanine, floxuridine, fludarabine, and cladribine.

Examples of chemotherapeutic agents that are natural products include actinomycin D, bleomycin, camptothecins, daunomycin, doxorubicin, etoposide, mitomycin C, paclitaxel, taxoteredocetaxel, tenisposide, vincristine, vinblastine, vinorelbine, idarubicin, mitoxantrone, mithramycin and deoxycoformycin.

Examples of hormonal agents include estrogen receptor antagonists such as tamoxifen and fluvestrant, aromatase inhibitors such as anastrozole, androgen receptor antagonists such as cyproterone and flutamine, as well as gonadotropin release hormone agonists such as leuprolide. Examples of anti-inflammatory drugs include adrenocorticoids such as prednisone, and nonsteroidal anti-inflammatory drugs such as sulindac or celecoxib. Examples of molecular targeted drugs include monoclonal antibodies such as rituximab, cetuximab, trastuzumab and small molecules such as imatinib, erlotinib, ortizumib. Examples of anti-angiogenic drugs include thalidomide and bevacizimab. Examples of the aforesaid miscellaneous chemotherapeutic agents include mitotane, arsenic trioxide, tretinoin, thalidomide, levamisole, L-asparaginase and hydroxyurea.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

REFERENCES

1. Heron M. Deaths: leading causes for 2007. *Natl Vital Stat Rep.* 2011, 59, 1-95.
2. Bayes M, Rabasseda X, Prous J R. *Gateways to clinical trials.* Methods Find Exp Clin Pharmacol. 2006, 28, 121-42.
3. Arifin D Y, Lee K Y, Wang C H. *Chemotherapeutic drug transport to brain tumor.* J Control Release. 2009, 137, 203-10.
4. Stoehlmacher J, Lenz H J. *Cyclooxygenase-2 inhibitors in colorectal cancer.* Semin Oncol. 200, 30 (3 Suppl 6), 10-6
5. Tinsley H N, Gary B D, Keeton A B, Zhang W, Abadi A H, Reynolds R C, Piazza G A. *Sulindac sulfide selectively inhibits growth and induces apoptosis of human breast tumor cells by phosphodiesterase 5 inhibition, elevation of cyclic GMP, and activation of protein kinase G.* Mol Cancer Ther. 2009, 8, 3331-40.
6. Tinsley H N, Gary B D, Thaiparambil J, Li N, Lu W, Li Y, Maxuitenko Y Y, Keeton A B, Piazza G A. *Colon tumor cell growth-inhibitory activity of sulindac sulfide and other nonsteroidal anti-inflammatory drugs is associated with phosphodiesterase 5 inhibition.* Cancer Prev Res (Phila.). 2010, 3, 1303-13.
7. Whitehead C M, Earle K A, Fetter J, Xu S, Hartman T, Chan D C, Zhao T L, Piazza G, Klein-Szanto A J, Pamukcu R, Alila H, Bunn P A Jr, Thompson W J. *Exisulind-induced apoptosis in a non-small cell lung cancer orthotopic lung tumor model augments docetaxel treatment and contributes to increased survival.* Mol Cancer Ther. 2003, 2, 479-88
8. Klein T, Eltze M, Grebe T, Hatzelmann A, Kömhoff M. Celecoxib dilates guinea-pig coronaries and rat aortic rings and amplifies NO/cGMP signaling by PDE5 inhibition Cardiovasc Res. 2007, 75, 390-7.

What is claimed is:
1. The compound 4-(3-tert-butyl-5-(2,4-dichlorophenyl)-4,5-dihydropyrazol-1-yl)benzoic acid and pharmaceutically acceptable salts thereof, prodrugs and solvates thereof.
2. The compound according to claim 1 being 4-(3-tert-butyl-5-(2,4-dichlorophenyl)-4,5-dihydropyrazol-1-yl)benzoic acid or a pharmaceutically acceptable salt thereof.

3. The compound according to claim 1 being 4-(3-tert-butyl-5-(2,4-dichlorophenyl)-4,5-dihydropyrazol-1-yl)benzoic acid or a solvate thereof.

4. The compound according to claim 1 being 4-(3-tert-butyl-5-(2,4-dichlorophenyl)-4,5-dihydropyrazol-1-yl)benzoic acid.

5. A pharmaceutical composition comprising the compound of claim 1, a pharmaceutically acceptable salt thereof, or a mixture thereof and a pharmaceutically acceptable carrier.

6. A pharmaceutical composition comprising the compound of claim 1, a solvate thereof or a mixture thereof and a pharmaceutically acceptable carrier.

7. A pharmaceutical composition comprising the compound of claim 1 and a pharmaceutically acceptable carrier.

8. A pharmaceutical composition comprising the compound of claim 1, a pharmaceutically acceptable salt thereof, a prodrug thereof, a solvate thereof or a mixture thereof and a pharmaceutically acceptable carrier.

\* \* \* \* \*